(12) United States Patent
Zhang et al.

(10) Patent No.: US 12,148,888 B2
(45) Date of Patent: *Nov. 19, 2024

(54) ELECTROLYTES FOR ELECTROCHEMICAL ENERGY STORAGE

(71) Applicant: UCHICAGO ARGONNE, LLC, Chicago, IL (US)

(72) Inventors: Zhengcheng Zhang, Naperville, IL (US); Noah Mark Johnson, Westmont, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,668

(22) Filed: Apr. 12, 2023

(65) Prior Publication Data

US 2023/0275272 A1 Aug. 31, 2023

Related U.S. Application Data

(63) Continuation of application No. 16/828,748, filed on Mar. 24, 2020, now Pat. No. 11,735,772.

(51) Int. Cl.
| | | |
|---|---|---|
| *H01M 10/0567* | (2010.01) | |
| *H01M 10/054* | (2010.01) | |
| *H01M 10/0568* | (2010.01) | |
| *H01M 10/0569* | (2010.01) | |
| *C07C 259/10* | (2006.01) | |

(52) U.S. Cl.
CPC ..... *H01M 10/0567* (2013.01); *H01M 10/054* (2013.01); *H01M 10/0568* (2013.01); *H01M 10/0569* (2013.01); *C07C 259/10* (2013.01); *H01M 2300/0037* (2013.01)

(58) Field of Classification Search
CPC ......... H01M 10/0567; H01M 10/0568; H01M 10/0569; H01M 10/054; H01M 2300/0037
See application file for complete search history.

(56) References Cited

U.S. PATENT DOCUMENTS

| | | |
|---|---|---|
| 9,287,597 B2 | 3/2016 | Friesen et al. |
| 2007/0020527 A1 | 1/2007 | Ehrismann et al. |
| 2010/0209780 A1 | 8/2010 | Muldoon et al. |
| 2015/0221999 A1 | 8/2015 | Friesen et al. |
| 2019/0013548 A1 | 1/2019 | Halalay et al. |
| 2019/0379039 A1 | 12/2019 | Zhamu et al. |
| 2020/0099090 A1 | 3/2020 | Li et al. |

FOREIGN PATENT DOCUMENTS

WO WO-2018/214972 A1 11/2018

OTHER PUBLICATIONS

Final Office Action on U.S. Appl. No. 16/828,748 dated Dec. 27, 2021.
Non-Final Office Action on U.S. Appl. No. 16/828,748 dated Jun. 8, 2022.
Non-Final Office Action on U.S. Appl. No. 16/828,748 dated Sep. 15, 2022.
Non-Final Office Action on U.S. Appl. No. 16/828,748 dated Sep. 20, 2021.

(Continued)

*Primary Examiner* — Laura Weiner
(74) *Attorney, Agent, or Firm* — Foley & Lardner LLP

(57) ABSTRACT

An electrochemical device includes an electrolyte having a hydroxamate or N-hydroxyamide compound.

13 Claims, 8 Drawing Sheets

(56) References Cited

OTHER PUBLICATIONS

Notice of Allowance on U.S. Appl. No. 16/828,748 dated Jan. 25, 2023.
Notice of Allowance on U.S. Appl. No. 16/828,748 dated Apr. 3, 2023.
Rericha, et al., "On interpretation of a missing spectral band, IR spectra of acidic salts of benzohydroxamic acid," Spectrochimica Acta Part A: Molecular and Biomolecular Spectroscopy, vol. 61, Issue 8, 2005, pp. 1899-1903.

ELECTROLYTES FOR ELECTROCHEMICAL ENERGY STORAGE

CROSS-REFERENCE TO RELATED APPLICATIONS

This application is a continuation of and claims priority to U.S. patent application Ser. No. 16/828,748, filed Mar. 24, 2020, which is now U.S. Pat. No. 11,735,772, the contents of which are incorporated herein by reference in its entirety.

GOVERNMENT RIGHTS

This invention was made with government support under Contract No. DE-AC02-06CH11357 awarded by the United States Department of Energy to UChicago Argonne, LLC, operator of Argonne National Laboratory. The government has certain rights in the invention.

FIELD

The present technology is generally related to lithium or sodium ion battery and improving their performance through the use of additives to the electrolyte. More specifically, it is related to the addition of hydroxamates or N-hydroxide-amide compounds for use in electrolytes for lithium or sodium ion batteries.

BACKGROUND

Electrodes made from transition metal oxides are commonly used in high-energy batteries. However, these electrodes are unstable under extreme conditions, such as at high temperatures and voltages. The interface between the electrode and the electrolyte is the dominant site of instability, such as electrolyte oxidation, undesirable phase transitions, and dissolution of transition metals. Current methods used to solve this problem fall into three broad categories. First, the counter electrode can be protected from the negative effects of the cathode degradation, by creating a more protective surface-electrolyte interphase (SEI), or by preventing the TMs from reaching the anode. Second, the reactivity of the electrolyte can be reduced, by changing the salts or using additives to prevent HF generation, or by using alternative solvents that are resistant to oxidation. Third, the cathode itself can be made more stable, by changing its composition, modifying the surface, or using additives that can form a stable interface.

While much progress has been made, operation under high temperatures and voltages remains a challenge. The first two approaches mitigate the problems, but they do not resolve them sufficiently for long-term use. Changing the composition of the cathode increases stability at the cost of energy density, and surface modifications inhibit kinetics and are expensive. Using additives to form a stable interface would be the optimal approach, but so far creating a uniform film, like is commonly done on graphite anodes, and hasn't been consistently achieved.

SUMMARY

In one aspect, an electrochemical device is provided that includes an electrolyte comprising a hydroxamate or N-hydroxyamide compound. The hydroxamate or N-hydroxyamide compound may be represented in some embodiments as a compound of Formula I:

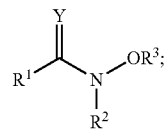

(I)

wherein:
Y is O, S, or Se;
$R^1$ is $R^4$, alkoxy, alkenyl, alkenylalkyl, aryl, cycloalkyl, heterocyclyl, heterocyclylalkyl, aralkyl, heteroaryl, heteroaralkyl, silyl, linear carbonate group, cyclic carbonate group, cyano group, or oligo (ethylene glycol);
$R^2$ is H, alkyl, alkoxy, alkenyl, alkenylalkyl, aryl, cycloalkyl, heterocyclyl, heterocyclylalkyl, aralkyl, heteroaryl, heteroaralkyl, silyl, linear carbonate group, cyclic carbonate group, cyano group, or oligo (ethylene glycol);
$R^3$ is H, silyl, $Li^+$, $Na^+$, $K^+$, or $NH_4^+$; and
$R^4$ is unsubstituted $C_1$-$C_3$ alkyl, or substituted alkyl.

In any of the above embodiments, the electrochemical device may be a lithium ion battery, a sodium ion battery, or a potassium ion battery.

DETAILED DESCRIPTION

Figure 1:
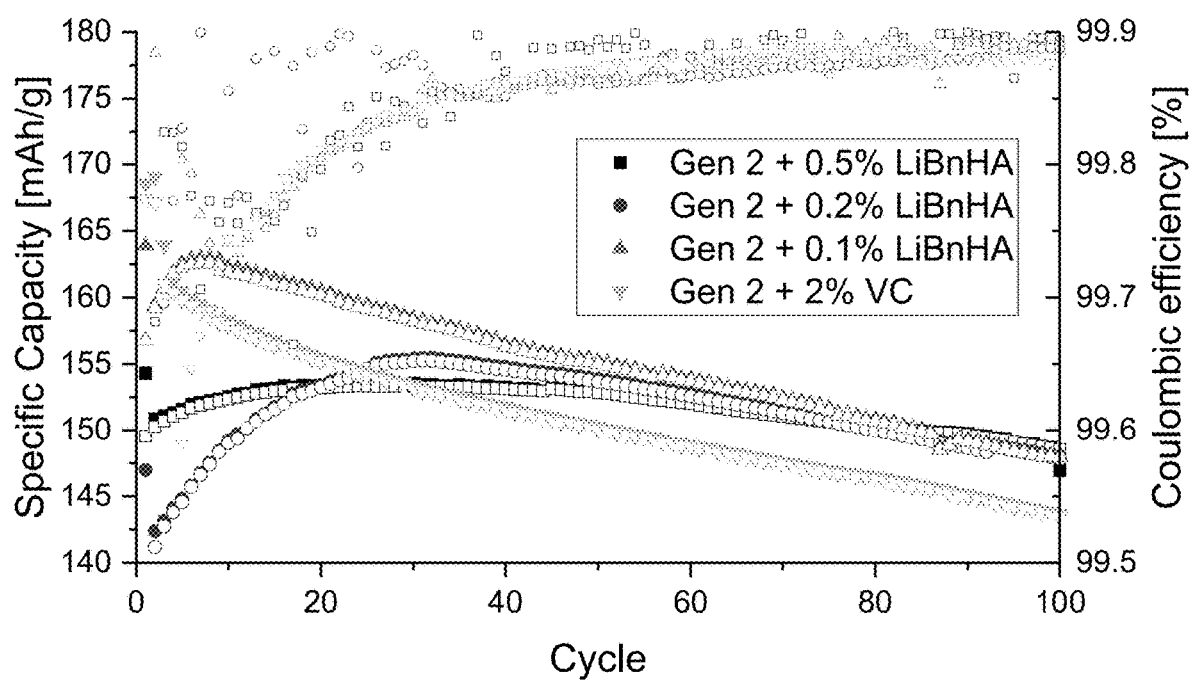
FIG. 1 is a dual axis graph for specific capacity and Coulombic efficiency of cells prepared according to Example 1.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of examples, or illustrative language (e.g., "such as") provided herein, is intended merely to better illuminate the embodiments and does not pose a limitation on the scope of the claims unless otherwise stated. No language in the specification should be construed as indicating any non-claimed element as essential.

In general, "substituted" refers to an alkyl, alkenyl, alkynyl, aryl, or ether group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, "alkyl" groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Alkyl groups may be substituted or unsubstituted. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a perhaloalkyl group.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups may be substituted or unsubstituted. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups may be substituted or unsubstituted. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

As used herein, "aryl", or "aromatic," groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. The phrase "aryl groups" includes groups containing fused rings, such as fused aromatic-aliphatic ring systems (e.g., indanyl, tetrahydronaphthyl, and the like). Aryl groups may be substituted or unsubstituted.

It is known that in lithium and sodium ion batteries most degradation processes of the electrode start at the electrode/electrolyte interface. The degradation may be due to one or more gas evolution, electrolyte decomposition, migration soluble species from the election, re-precipitation of undesirable phases on an electrode, dissolution of the electrode, structural disordering in the electrode, micro-cracking of the electrode surface, corrosion of the current collector, oxidation of conductive particles in the electrode, and binder decomposition. These processes limit the longevity of the batteries, limit the usage conditions, and affect the available energy of electrochemical storage devices. Accordingly, impeding or preventing any of these processes may lead to improvements in battery performance.

It has now been found that by incorporating small amounts of hydroxamate or N-hydroxyamide compounds in a non-aqueous electrolyte of an electrochemical device, performance may be improved. The hydroxamate/N-hydroxideamide compounds generally may be represented by Formula (I):

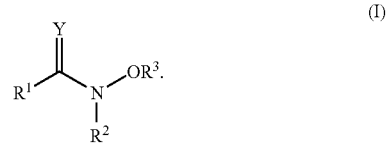

(I)

In Formula (I), Y may be O, S, or Se; $R^1$ may be $R^4$, alkoxy, alkenyl, alkenylalkyl, aryl, cycloalkyl, heterocyclyl, heterocyclylalkyl, aralkyl, heteroaryl, heteroaralkyl, silyl, linear carbonate group, cyclic carbonate group, cyano group, or oligo (ethylene glycol); $R^2$ may be H, alkyl, alkoxy, alkenyl, alkenylalkyl, aryl, cycloalkyl, heterocyclyl, heterocyclylalkyl, aralkyl, heteroaryl, heteroaralkyl, silyl, linear carbonate group, cyclic carbonate group, cyano group, or oligo (ethylene glycol); $R^3$ may be H, silyl, $Li^+$, $Na^+$, $K^+$, or $NH_4^+$; and $R^4$ may be unsubstituted $C_1$-$C_3$ alkyl, or substituted alkyl.

As used herein, a non-aqueous electrolyte contains less than an appreciable amount of water and are preferably anhydrous.

Without being bound by theory, it is believed that the hydroxamate functionality coordinates to transition metals (on the surface of the electrode) in a bidentate fashion. The hydroxamate compound then forms a protective layer over the surface of the electrode through chemisorption, thereby reducing surface reactivity of the electrode and stabilizing it against degradation pathways. The hydroxamate or N-hydroxyamide compounds appear to provide for high specificity in chelating/protecting the surface transition metal in the electrode, and they directly target the cathode materials through chemisorption, independent of voltage, solvent, and other additives. They can also be used in combination with other, more common additives, such as vinyl carbonate, vinylene carbonate (VC), fluoroethylene carbonate (FEC), difluoroethylene carbonate (DFEC), fluorinated propylene carbonate (TFPC), lithium difluoro(oxalato)borate (LiDFOB), lithium bis(oxalato)borate (LiBOB), 1,3-propane sultone (PS), 1,3-propene sultone, and tris-(trimethylsilyl) phosphite, cyclophosphazene compounds, cyanide compounds including malononitrile ($CNCH_2CN$), succinonitrile ($CNCH_2CH_2CN$), fumaronitrile (CNCH=CHCN), adiponitrile ($CNCH_2CH_2CH_2CN$), and trinitriles including 1,3,5-pentanetricarbonitrile, 1,3,6-hexanetricarbonitrile, and many others.

In some embodiments of Formula (I), $R^1$ may be methyl, ethyl, n-propyl, iso-propyl, substituted alkyl, or $C_6$-$C_{20}$ aryl. For example, R may be methyl, ethyl, n-propyl, iso-propyl, substituted $C_1$-$C_{20}$-alkyl, unsubstituted phenyl, substituted phenyl, unsubstituted naphthyl, substituted naphthyl, unsubstituted heterocyclyl, substituted heterocyclyl, unsubstituted heterocyclylalkyl, or substituted heterocyclylalkyl in other embodiments, $R^1$ may be —$CH_2C(O)NH(OH)$, —$O(CH_2CH_2O)_qCH_3$, —$CH_2P(O(OR^5)_2$, wherein each $R^5$ is individually alkyl, —$CH_2(CF)_qCF_3$, 2-furanyl, 3-furanyl, phenyl, or ethylene carbonate, wherein each q is from 0 to 20, inclusive.

In some embodiments of Formula (I), $R^2$ may be H, unsubstituted $C_1$-$C_{20}$ alkyl, substituted $C_1$-$C_{20}$ alkyl, unsubstituted $C_1$-$C_{20}$ alkenylalkyl, substituted $C_1$-$C_{20}$ alkenylalkyl, unsubstituted phenyl, substituted phenyl, unsubstituted naphthyl, substituted naphthyl unsubstituted heterocyclyl, substituted heterocyclyl, unsubstituted heterocyclylalkyl, substituted heterocyclylalkyl, or trimethylsilyl. In other embodiments, $R^2$ may be H, methyl, ethyl, n-propyl, iso-propyl, n-butyl, sec-butyl, t-butyl, n-pentyl, n-hexyl, n-heptyl, trimethylsilyl, triethylsilyl, perfluoroethyl, perfluoropropyl, or 2-allyl. In other embodiments, $R^2$ may be —$CH_2C(O)NH(OH)$ or —$CH_2P(O)(OR^5)_2$, wherein each $R^5$ is individually alkyl, —$CH_2(CF_2)_qCF_3$, 2-furanyl, 3-furanyl, phenyl, or ethylene carbonate.

In some embodiments of Formula (I), $R^3$ may be H or $Li^+$.
In some embodiments of Formula (I), Y is O.
In some embodiments of Formula (I), the compound represented as Formula I is:

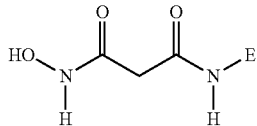

A

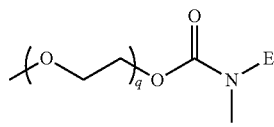

B

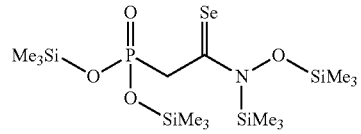

C

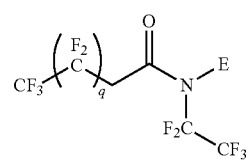

D

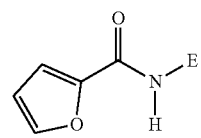

E

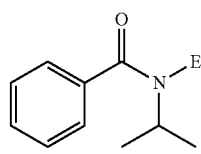

F

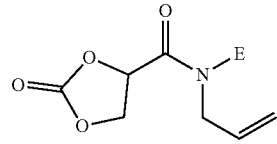

G

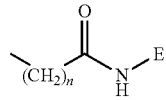

H

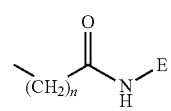

I

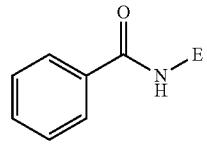

J

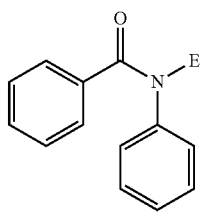

K

-continued

L

M

N

O

P

Q

R

S

T

-continued

U

V

W

X

Y

Z

AA

AB

AC

AD

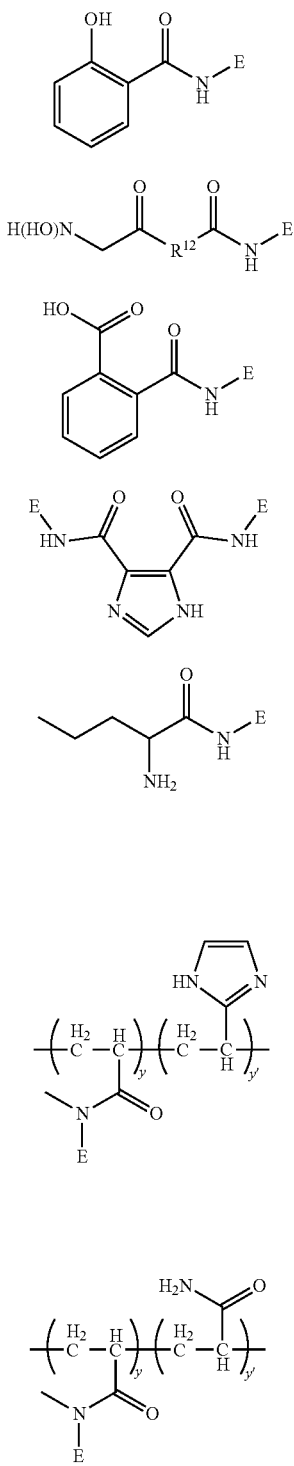

wherein each E is independently —OH, —O⁻Li⁺, —O⁻Na⁺, —O⁻K⁺, or —O⁻NH₄⁺, $R^{10}$ is H, Cl, NO₂, or OCH₃, $R^{11}$ is H, Cl, or NH₂, $R^{12}$ is absent or CH₂, each n is 0, 1, or 2, each q is from 0 to 20, inclusive, y and y' represent polymer repeat units. In some embodiments, y and y' are from 10 to 200. In any of the compounds described herein, the racemic structures are drawn, but for any chiral center the orientation may be R— or S—.

The compound of structure:

AF is also known as lithium benzohydroxamate (LiBnHA).

In any of the above embodiments, the amount of the hydroxamate, N-hydroxyamide, or compound of Formula (I) is from 0.005 M to 2 M, based upon the total volume of the electrolyte. This includes from 0.01 M to 1.5 M, 0.01 M to 1.5 M, 0.01 M to 1 M, 0.01 M to 0.5 M, 0.01 M to 0.1 M, 0.1 M to 2 M, 0.1 M to 1.5 M, 0.1 M to 1 M, or 0.1 M to 0.5 M.

In any of the above embodiments, the electrolyte may further include a lithium or sodium salt. If the cell is a lithium ion cell, the electrolyte may contain a lithium salt. If the cell is a sodium ion cell, the electrolyte may contain a sodium salt. Illustrative lithium salts include, but are not limited to lithium alkyl fluorophosphates; lithium alkyl fluoroborates; lithium 4,5-dicyano-2-(trifluoromethyl)imidazole; lithium 4,5-dicyano-2-methylimidazole; trilithium 2,2',2''-tris(trifluoromethyl)benzotris(imidazolate); LiN(CN)₂; Li(CF₃CO₂); Li(C₂F₅CO₂); LiCF₃SO₃; LiCH₃SO₃; LiN(SO₂CF₃)₂; LiN(SO₂F)₂; LiC(CF₃SO₂)₃; LiN(SO₂C₂F₅)₂; LiClO₄; LiBF₄; LiAsF₆; LiPF₆; LiBF₂(C₂O₄), LiB(C₂O₄)₂, LiPF₂(C₂O₄)₂, LiPF₄(C₂O₄), LiAsF₆, CsF, CsPF₆, LiN(SO₂CF₃)₂, LiN(SO₂F)₂, Li₂(B₁₂X₁₂₋ₚHₚ); Li₂(B₁₀X₁₀₋ₚ'Hₚ'); or a mixture of any two or more thereof, wherein X may be independently at each occurrence a halogen, p may be 0, 1, 2, 3, 4, 5, 6, 7, 8, 9, 10, 11, or 12, and p' may be 0, 1, 2, 3, 4, 5, 6, 7, 8, 9, or 10. In some embodiments, the salt may be LiPF₆, LiBF₄, LiN(SO₂CF₃)₂, or LiN(SO₂F)₂. Where the salt is a sodium salt any of the above may be used as the sodium salt instead of the lithium salt. The salt may be present in the electrolyte at any amount including from about 0.5 M to 5 M. This may include from about 1 M to about 2M.

In any of the above embodiments, the electrolytes may further include a solvent, which in some embodiments, is a polar aprotic solvent. Such polar aprotic solvents may include, but are not limited to, organic carbonates, fluorinated carbonates, ethers, fluorinated ethers, glymes, other sulfones, organic sulfates, esters, cyclic esters, fluorinated esters, nitriles, amides, dinitriles, fluorinated amides, carbamates, fluorinated carbamates, cyanoester compounds, pyrrolidinium-based ionic liquids, piperidinium-based ionic liquids, imidazolium-based ionic liquids, ammonium-based ionic liquids, phosphonium-based ionic liquids, or cyclic phosphonium-based ionic liquids. In some embodiments, the solvent may be a carbonate, a sulfone, a siloxane, a silane, an ether, an ester, a lactone, ionic liquids, any fluorinated derivatives thereof, or a blend of any two or more such solvents. For example, the solvent may include one or more of dimethyl carbonate, ethyl methyl carbonate (EMC), diethyl carbonate, methyl propyl carbonate, ethyl propyl carbonate, dipropyl carbonate, dimethoxyethane, triglyme, propylene carbonate (PC), dimethylvinylene carbonate, tetraethyleneglycol, dimethyl ether, polyethylene glycols, γ-butyrolactone, ethylene carbonate (EC), difluoroethylene carbonate (DFEC), fluoroethylmethylcarbonate (FEMC), bis(trifluoroethyl) carbonate, bis(pentafluoropropyl) carbonate, trifluoroethyl methyl carbonate, pentafluoroethyl methyl carbonate, heptafluoropropyl methyl carbonate, perfluorobutyl methyl carbonate, trifluoroethyl ethyl carbonate, pentafluoroethyl ethyl carbonate, heptafluoropropyl ethyl carbonate, or perfluorobutyl ethyl carbonate, as well as fluorinated solvents and fluorinated version of any of the foregoing solvents with being just two examples. In some embodiments, the non-aqueous solvent is one or more of PC, EC, EMC, DFEC, or FEMC. In some embodiments, the solvent is a piperidinium-based ionic liquid or an imidazolium-based ionic liquid.

The electrochemical devices may also include an anode and a cathode, and, in some instances a separator between the anode and the cathode. Illustrative cathode materials include, but are not limited to, any of a wide variety of lithium-containing cathode active materials including lithium nickel-manganese-cobalt oxide compositions, and the like. In some embodiments, the cathode active material includes, but is not limited to a spinel, olivine, $Li_{1+w}Mn_xNi_y$-$Co_zO_2$, $LiMn_xNi_yO_4$, or $a'Li_2MnO_3 \cdot (1-a')LiMO_2$, wherein $0<w<1$, $0\leq x<1$, $0\leq y<1$, $0\leq z<1$, and $x+y+z=1$; $0\leq x'<2$, $0\leq y'<2$, and $x'+y'=2$; and $0\leq a'<2$. As used herein, a "spinel" refers to a manganese-based spinel such as, $Li_{1+x}Mn_{2-y}Me_zO_{4-h}A_k$, wherein Me is Al, Mg, Ti, B, Ga, Si, Ni, or Co; A is S or F; and wherein $0\leq x\leq 0.5$, $0\leq y\leq 0.5$, $0\leq z\leq 0.5$, $0\leq h\leq 0.5$, and $0\leq k\leq 0.5$. The term "olivine" refers to an iron-based olivine such as, $LiFe_{1-x}Me_yPO_{4-h}A_k$, wherein Me is Al, Mg, Ti, B, Ga, Si, Ni, or Co; A is S or F; and wherein $0\leq x\leq 0.5$, $0\leq y\leq 0.5$, $0\leq h\leq 0.5$, and $0\leq k\leq 0$. Other cathode active materials may include any of the following, alone or in combination with any of the cathode active materials described herein, a spinel, an olivine, a carbon-coated olivine $LiFePO_4$, $LiMn_{0.5}Ni_{0.5}O_2$, $LiCoO_2$, $LiNiO_2$, $LiNi_{1-x}Co_yMe_zO_2$, $LiNi_\alpha Mn_\beta Co_\gamma O_2$, $LiMn_2O_4$, $LiFeO_2$, $LiNi_{0.5}Me_{1.5}O_4$, $Li_{1+x}Ni_hMn_kCo_lMe^2_yO_{2-z}F_{z'}$, $VO_2$ or $E_{x''}F_2(Me_3O_4)_3$, $LiNi_mMn_nO_4$, wherein Me is Al, Mg, Ti, B, Ga, Si, Mn, or Co; $Me^2$ is Mg, Zn, Al, Ga, B, Zr, or Ti; E is Li, Ag, Cu, Na, Mn, Fe, Co, Ni, or Zn; F is Ti, V, Cr, Fe, or Zr; wherein $0\leq x\leq 0.3$; $0\leq y\leq 0.5$; $0\leq z\leq 0.5$; $0\leq m\leq 2$; $0\leq n\leq 2$; $0\leq x'\leq 0.4$; $0\leq \alpha\leq 1$; $0\leq \beta\leq 1$; $0\leq \gamma\leq 1$; $0\leq h\leq 1$; $0\leq k\leq 1$; $0\leq l\leq 1$; $0\leq y'\leq 0.4$; $0\leq z'\leq 0.4$; and $0\leq x''\leq 3$; with the proviso that at least one of h, k and l is greater than 0. Where the composition is $LiNi_{0.6}Mn_{0.2}Co_{0.2}O_2$, the material is known as NMC622. The cathode active material may also be accompanied by a conductive carbon material such as natural graphite, synthetic graphite, hard carbon, amorphous carbon, soft carbon, mesocarbon microbeads (MCMB), acetylene black, Ketjen black, carbon black, mesoporous carbon, porous carbon matrix, carbon nanotube, carbon nanofiber, and graphene.

The hydroxamate/N-hydroxideamide compounds may be for application in the lithium cathode active materials described above. They may also be used in sodium and potassium ion batteries as well, where sodium or potassium salts of the above lithium salts are used in the electrolyte, and where sodium or potassium counterparts are substituted for the illustrated lithium active materials. In some embodiments, where the electrochemical device is a sodium ion battery, the cathode active material may include one or more of $NaNi_{0.5}Mn_{0.5}O_2$, $Na_xMn_{1/3}Fe_{1/3}Cu_{1/6}Mg_{1/6}O_2$, $NaMn_{0.48}Ni_{0.2}Fe_{0.3}Mg_{0.02}Mg_{1/6}O_2$, $Na_{0.85}Li_{0.1}Ni_{0.175}Mn_{0.525}Fe_{0.2}O_2$, $0.5Li_2MnO_3 \cdot 0.5LiMn_{0.42}Ni_{0.42}Co_{0.16}O_2$, $Na_{2/3}[Fe_{1/2}Mn_{1/2}]O_2$, $Na_{0.7}Ni_{0.3}Mn_{0.59}Co_{0.1}Cu_{0.01}O_2$, $Na_{0.67}Mn_{0.67}Ni_{0.33-x}Mg_xO_2$ ($0\leq x\leq 0.33$), $Na_xCo_{0.1}Mn_{0.9}O_2$, $Na_{0.6}MnO_2$, $Li_2MnO_3$ (Li—O'3), $Na_2RuO_3$, $Na(Li_{1/3}M_{2/3})O_2$, $Na_{0.6}Li_{0.2}Mn_{0.8}O_2$, $Na_{2/3}[Mg_{0.28}Mn_{0.72}]O_2$, or $Na_{0.5}Ni_{0.25}Mn_{0.75}O_2$. In some embodiments, where the electrochemical device is a potassium ion battery, the potassium active material may include one or more of $KMnO_2$, $KCoO_2$, TiS, $K[Fe_{0.5}Mn_{0.5}]O_2$, $KFe[Fe(CN_6)]$, $K_2Fe[Fe(CN_6)]$, $KMn[Fe(CN_6)]$, $K[Fe(PO_4)]$, $KVPO_4F$, $KVOPO_4$, $K_3V_2(PO_4)_3$, $K_3Ti_2(PO_4)_3$, $KFeSO_4F$, or $K_2C_6O_6$.

The cathode may be further stabilized by surface coating the active particles with a material that can neutralize acid or otherwise lessen or prevent leaching of the transition metal ions. Hence the cathodes can also comprise a surface coating of a metal oxide or fluoride such as $ZrO_2$, $TiO_2$, $ZnO_2$, $WO_3$, $Al_2O_3$, MgO, $SiO_2$, $SnO_2$, $AlPO_4$, $Al(OH)_3$, $AlF_3$, $ZnF_2$, $MgF_2$, $TiF_4$, $ZrF_4$, a mixture of any two or more thereof, of any other suitable metal oxide or fluoride. The coating can be applied to a carbon-coated cathode. The cathode may be further stabilized by surface coating the active particles with polymer materials. Examples of polymer coating materials include, but not limited to, polysiloxanes, polyethylene glycol, or poly(3,4-ethylenedioxythiophene) polystyrene sulfonate, a mixture of any two or more polymers.

Illustrative anode materials include, but are not limited to, materials that may reversibly absorb or release lithium-ions or sodium-ions, preferably, for example, a material including artificial graphite, natural graphite, silicon, and graphitized carbon fiber amorphous carbon. Lithium or sodium metal also can be used as an anode active material.

Illustrative separator materials include, but are not limited to, a microporous or modified polymer separator. Illustrative separators include, but are not limited to, Celgard® 2325, Celgard® 2400, Celgard® 3501, and glass fiber separators.

In any of the above embodiments, the electrochemical device may be a lithium ion battery or a sodium ion battery.

In another aspect, a cathode for a lithium-ion, sodium-ion, or potassium-ion battery is provided, where the cathode contains particles of a cathode active material, as defined herein, which have been treated with a hydroxamate/N-hydroxideamide compound, as described herein. Such cathodes may be prepared by mixing the particles of the cathode active material with the hydroxamate/N-hydroxideamide compound in a suspension or slurry with a suspending liquid, then isolating the treated particles from the suspension liquid and drying prior to assembling the electrode. The hydroxamate/N-hydroxideamide compound is present in the suspending liquid from about 0.005 M to 2 M, based upon the total volume of the suspending liquid. This includes from 0.01 M to 1.5 M, 0.01 M to 1.5 M, 0.01 M to 1 M, 0.01 M to 0.5 M, 0.01 M to 0.1 M, 0.1 M to 2 M, 0.1 M to 1.5 M, 0.1 M to 1 M, or 0.1 M to 0.5 M.

Illustrative suspending liquids include, but are not limited to, water, alcoholsorganic carbonates, ethers, cyclic ethers, glymes, other sulfones, organic sulfates, esters, cyclic esters, ketones, nitriles, amides, nitriles, dinitriles, carbamates, cyanoester compounds, aromatic hydrocarbons, linear and branched hydrocarbons, and halogenated hydrocarbons.

The electrodes are prepared according to the understanding in the art with the use of a binder material, current collector, other conductive materials (i.e. carbonaceous materials), and additives.

In further aspect, a cathode for a lithium-ion, sodium-ion, or potassium-ion battery is provided, where the cathode is pretreated with a hydroxamate/N-hydroxideamide compound, as described herein, after formation of the cathode with particles of a cathode active material, as defined herein, a binder material, current collector, and other conductive materials (i.e. carbonaceous materials) as needed, and additives as needed.

The present invention, thus generally described, will be understood more readily by reference to the following examples, which are provided by way of illustration and are not intended to be limiting of the present invention.

EXAMPLES

Example 1. A cell was prepared using $LiNi_{0.6}Mn_{0.2}Co_{0.2}O_2$ as the cathode, and graphite as the anode, with an electrolyte of 1.2M $LiPF_6$ in a 3:7 ratio of ethylene carbonate (EC):ethyl methyl carbonate (EMC). In the figures, this electrolyte composition is known as "Gen 2." The cell was cycled at elevated temperature (55° C.) for 100 cycles at 1C. Under these conditions, test cells typically lose more than 13% of their starting capacity, with Coulombic efficiencies averaging 99.80%. Adding a state-of-the-art additive such as vinylene carbonate (VC) can improve this to 11% capacity loss and 99.85% Coulombic efficiency. However, when 0.5% (w/w) of lithium benzohydroxamate (LiBnHA) is added to the electrolyte instead, the capacity loss is reduced to less than 3%, with a Coulombic efficiency averaging 99.87%. See FIG. 1.

Figure 2A:
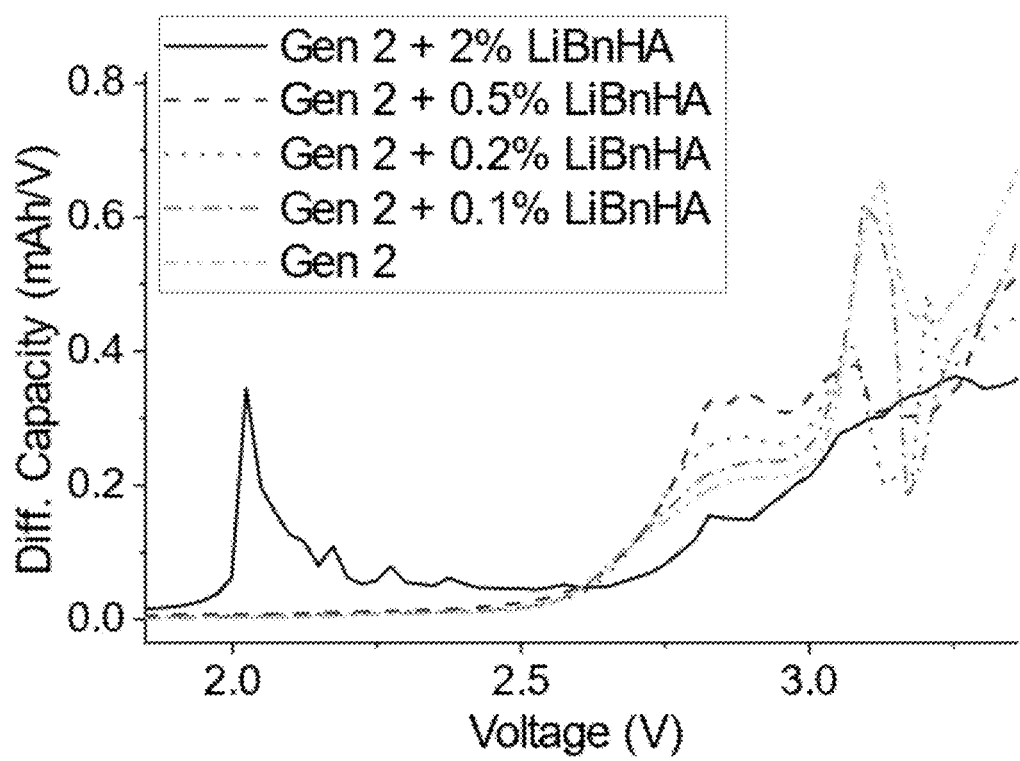
FIGS. 2A-2C illustrates the dQ/dV of different concentrations of LiBnHA at lower voltage ranges (FIG. 2A), higher voltage ranges (FIG. 2B), and the first and second (de)lithiation peaks for overpotential (FIG. 2C), according to Example 1.

Detailed analysis of the initial stabilization of the cell (commonly referred to as the "formation cycle") indicates that low concentrations of the additive will modulate the decomposition of EC, but there is no unique reduction product until high concentrations are reached (FIG. 2A).

Figure 2B:
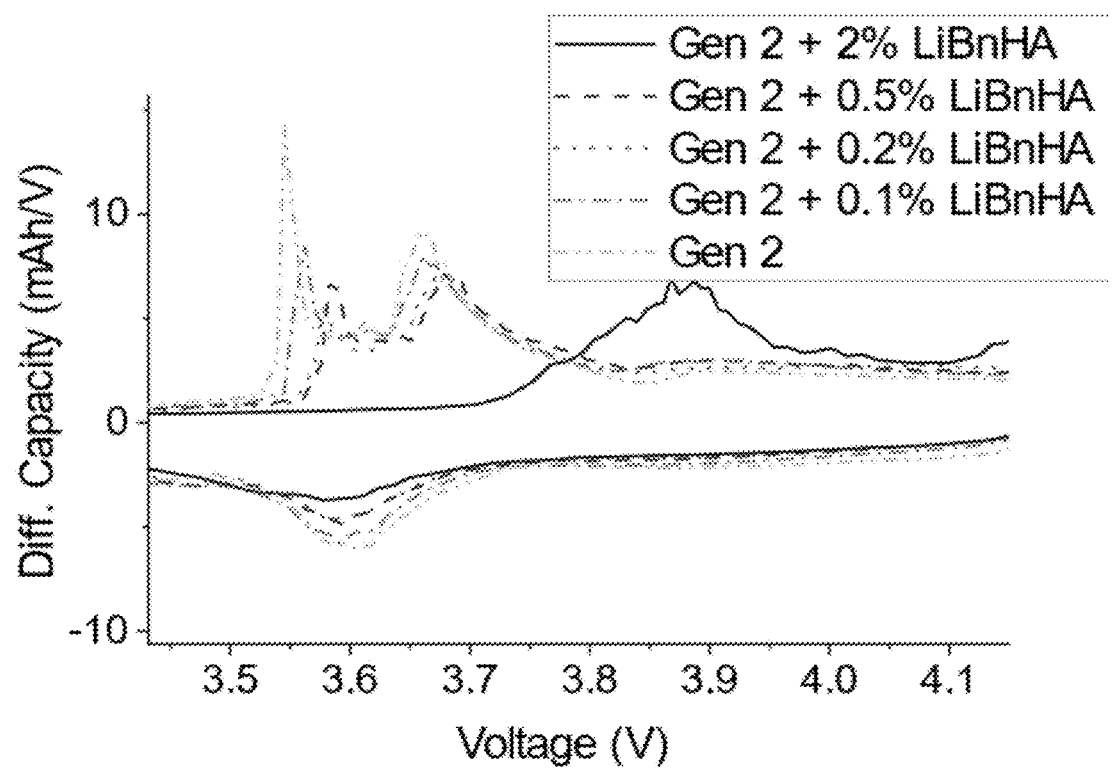
Figure 2C:
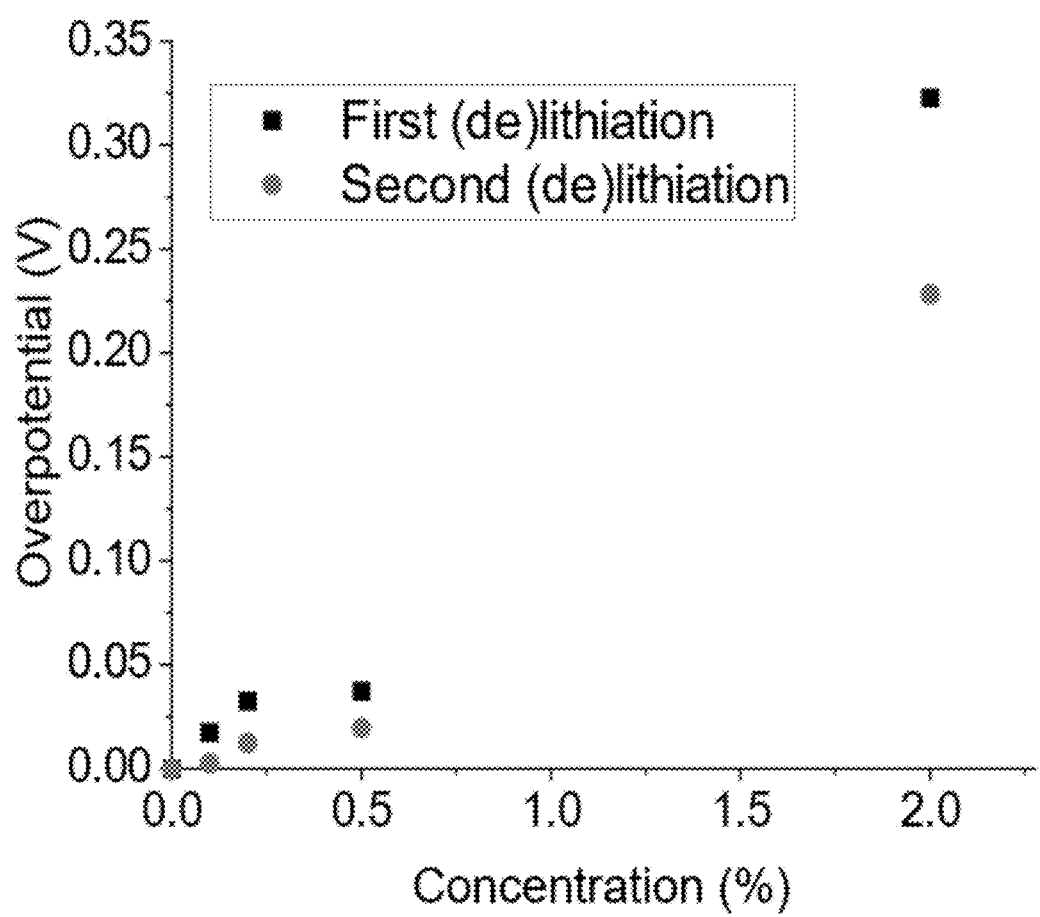
Figure 3:
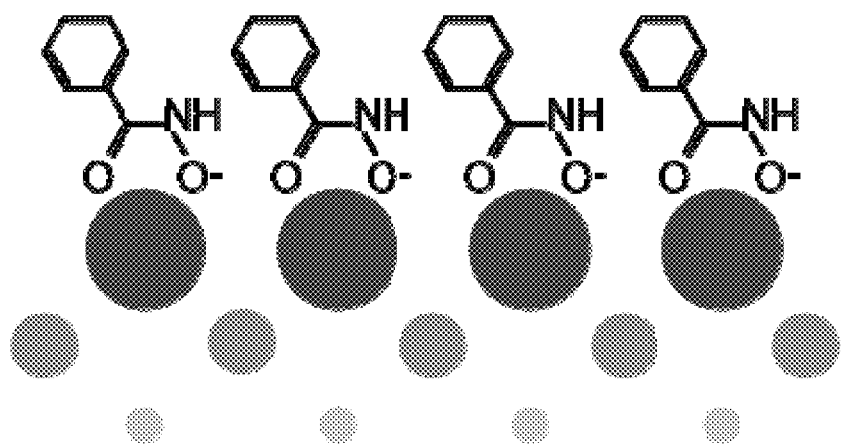
FIG. 3 is a diagram of the proposed mechanism of action.
Figure 4:
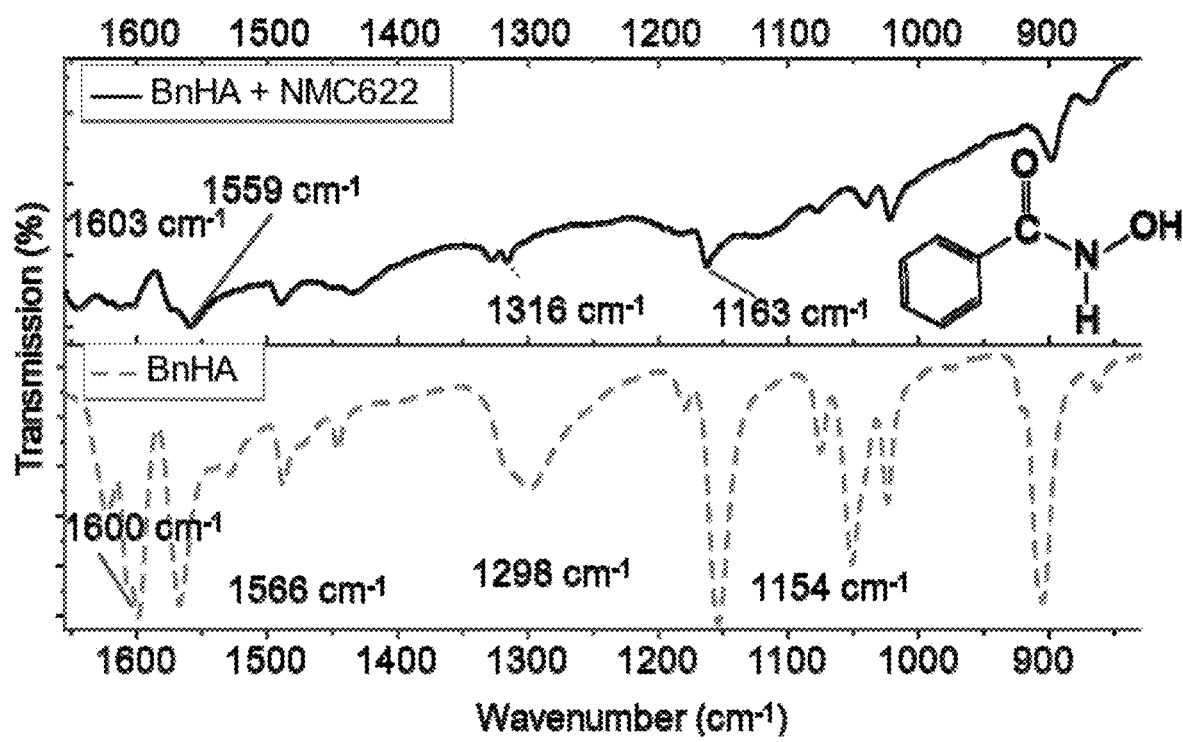
FIG. 4 is an FT-IR of benzohydroxamic acid in the solid state (bottom) and after stirring with pristine NMC622 powder (top), with relevant peaks highlighted.

However, even low concentrations of LiBnHA induce a significant overpotential on the initial (de)lithiation event (FIG. 2B). This overpotential is not linear at low concentrations, indicating some saturation mechanism (FIG. 2C). Low concentrations will saturate the surface of the cathode, forming a protective layer that is highly beneficial to long-term operation (FIG. 3). Excess material will react with the EC to help form a protective SEI. FT-IR analysis appears to confirm this hypothesis, with BnHA (benzylhydroxamic acid) showing the ability to chemisorb to pristine NMC622 by stirring in an acetonitrile solution (FIG. 4).

Figure 5:
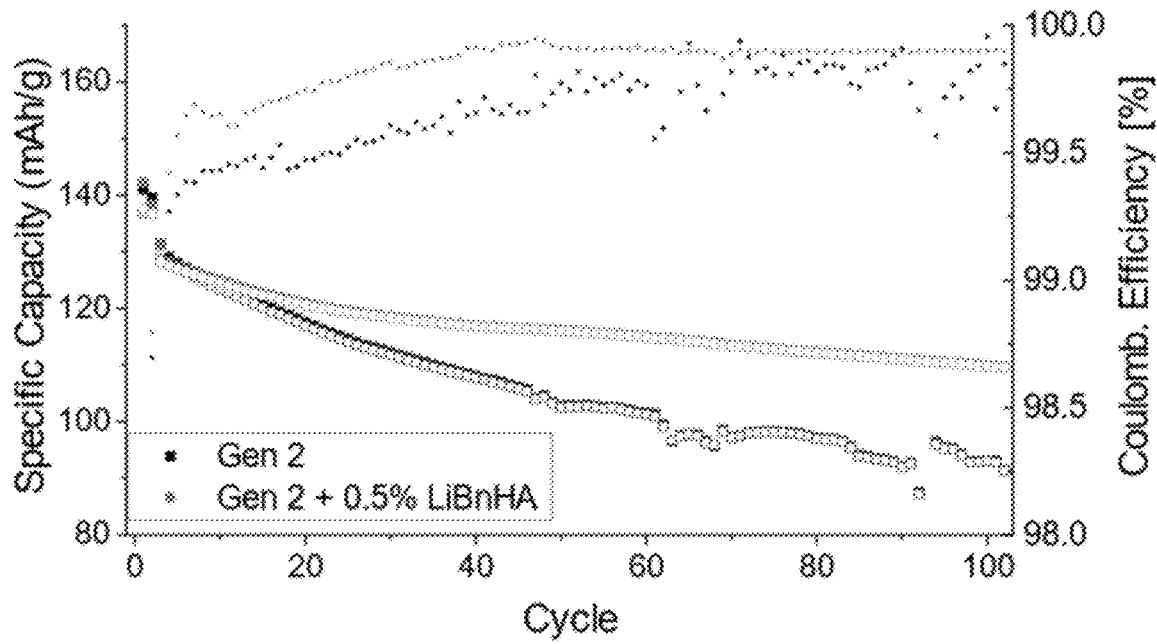
FIG. 5 is a dual axis graph for specific capacity and Coulombic efficiency of cells prepared according to Example 2.

Example 2. A cell was prepared using $LiCoO_2$ as the cathode, and graphite as the anode, with an electrolyte of 1.2M $LiPF_6$ in a 3:7 ratio of ethylene carbonate (EC):ethyl methyl carbonate (EMC). The cell was cycled at elevated temperature (55° C.) for 100 cycles at 1C between 3.0 V and 4.2V. Under these conditions, test cells typically lose more than 28% of their initial capacity, with an average Coulombic efficiency of 99.74%. However, when 0.5% (w/w) of lithium benzohydroxamate (LiBnHA) is added to the electrolyte instead, the capacity loss is reduced to less than 15%, with a Coulombic efficiency averaging 99.85%. Cells with electrolyte containing LiBnHA have final discharge capacities 20% higher than those with baseline electrolyte. See FIG. 5.

Figure 6:
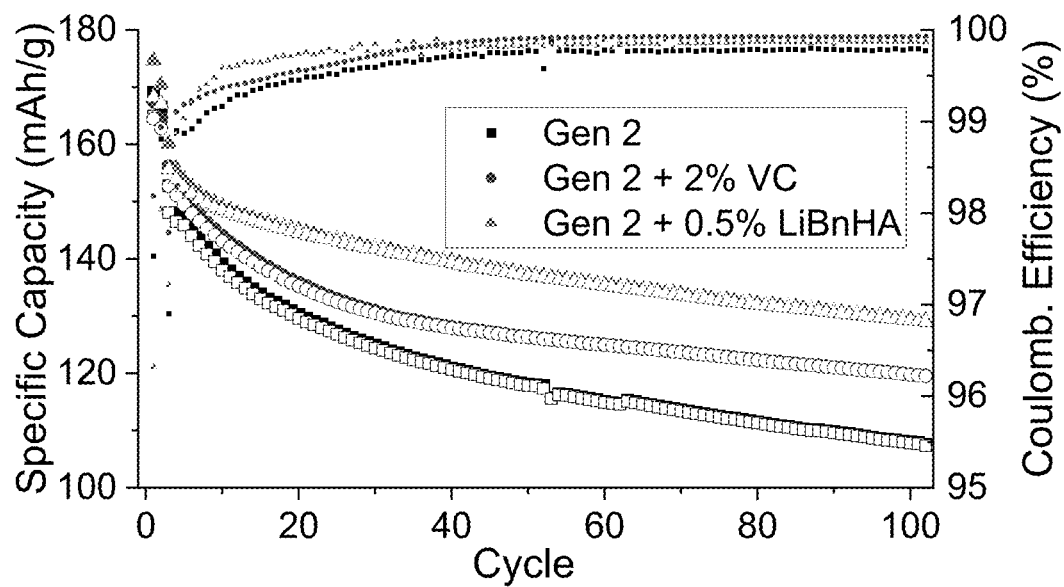
FIG. 6 is a dual axis graph for specific capacity and Coulombic efficiency of cells prepared according to Example 3.

Example 3. A cell was prepared using $LiCoO_2$ as the cathode, and graphite as the anode, with an electrolyte of 1.2M $LiPF_6$ in a 3:7 ratio of ethylene carbonate (EC):ethyl methyl carbonate (EMC). The cell was cycled at elevated temperature (55° C.) for 100 cycles at 1C between 3.0 V and 4.4V. Under these conditions, test cells typically lose more than 27% of their initial capacity, with an average coulombic efficiency of 99.65%. Adding a state-of-the-art additive such as vinylene carbonate (VC) can improve this to 21% capacity loss and 99.79% Coulombic efficiency. However, when 0.5% (w/w) of lithium benzohydroxamate (LiBnHA) is added to the electrolyte instead, the capacity loss is reduced to 17%, with a similar Coulombic efficiency averaging 99.79%. Cells with electrolyte containing LiBnHA have final discharge capacities 8% higher than those with VC, and 20% higher than those with no additives. See FIG. 6.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An electrochemical device comprising a cathode, an anode, and an electrolyte solution comprising a lithium or sodium salt, a polar aprotic solvent, and from 0.005 M to 2 M of a compound of Formula I:

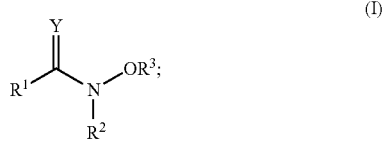

wherein:
- $R^1$ is a substituted or unsubstituted alkoxy, a substituted or unsubstituted $C_6$-$C_{20}$ aryl, a substituted or unsubstituted cycloalkyl, a substituted or unsubstituted heterocyclyl, a substituted or unsubstituted heterocyclylalkyl, a substituted or unsubstituted aralkyl, a substituted or unsubstituted heteroaryl, a substituted or unsubstituted heteroaralkyl, silyl, linear carbonate group, cyano group, oligo (ethylene glycol), $CH_2C(O)NH(OH)$, or —$CH_2P(O)(OR_5)_2$;
- $R^2$ is H, a substituted or unsubstituted alkyl, a substituted or unsubstituted alkoxy, a substituted or unsubstituted alkenyl, a substituted or unsubstituted alkenylalkyl, a substituted or unsubstituted aryl, a substituted or unsubstituted cycloalkyl, a substituted or unsubstituted heterocyclyl, a substituted or unsubstituted heterocyclylalkyl, a substituted or unsubstituted aralkyl, a substituted or unsubstituted heteroaryl, a substituted or unsubstituted heteroaralkyl, silyl, linear carbonate group, cyano group, or oligo (ethylene glycol);
- $R^3$ is H, silyl, $Li^+$, $Na^+$, $K^+$, or $NH_4^+$;
- each $R^5$ is individually a substituted or unsubstituted alkyl, —$CH_2(CF_2)_qCF_3$, 2-furanyl, 3-furanyl, phenyl, or ethylene carbonate, wherein each q is from 0 to 20, inclusive; and
- the polar aprotic solvent is selected from organic carbonates, fluorinated carbonates, ethers, fluorinated ethers, glymes, organic sulfates, esters, cyclic esters, fluorinated esters, nitriles, amides, dinitriles, fluorinated amides, carbamates, fluorinated carbamates, cyanoester compounds, or a mixture of any two or more thereof.

2. The electrochemical device of claim 1, wherein $R^1$ is unsubstituted phenyl, substituted phenyl, unsubstituted naphthyl, substituted naphthyl, unsubstituted heterocyclyl, substituted heterocyclyl, unsubstituted heterocyclylalkyl, or substituted heterocyclylalkyl.

3. The electrochemical device of claim 1, wherein $R^1$ is $CH_2C(O)NH(OH)$, $O(CH_2CH_2O)_qCH_3$, or —$CH_2P(O)(OR_5)_2$, wherein each $R^5$ is individually substituted or unsubstituted alkyl, —$CH_2(CF_2)_qCF_3$, 2-furanyl, 3-furanyl, phenyl, or ethylene carbonate, wherein each q is from 0 to 20, inclusive.

4. The electrochemical device of claim 1, wherein $R^2$ is H, unsubstituted $C_1$-$C_{20}$ alkyl, substituted $C_1$-$C_{20}$ alkyl, unsubstituted $C_1$-$C_{20}$ alkenylalkyl, substituted $C_1$-$C_{20}$ alkenylalkyl, unsubstituted phenyl, substituted phenyl, unsubstituted naphthyl, substituted naphthyl, unsubstituted heterocyclyl, substituted heterocyclyl, unsubstituted heterocyclylalkyl, substituted heterocyclylalkyl, or trimethylsilyl.

5. The electrochemical device of claim 1, wherein $R^2$ is H, methyl, ethyl, n-propyl, iso-propyl, n-butyl, sec-butyl, t-butyl, n-pentyl, n-hexyl, n-heptyl, trimethylsilyl, triethylsilyl, perfluoroethyl, perfluoropropyl, or 2-allyl.

6. The electrochemical device of claim 1, wherein $R^3$ is H or $Li^+$.

7. The electrochemical device of claim 1, wherein $R^3$ is H, silyl, $Li^+$, $Na^+$, or $K^+$.

8. The electrochemical device of claim 1, wherein the electrolyte solution comprises the lithium salt and the lithium salt comprises a lithium alkyl fluorophosphate; lithium alkyl fluoroborate; lithium 4,5-dicyano-2-(trifluoromethyl)imidazole; lithium 4,5-dicyano-2-methylimidazole; trilithium 2,2',2''-tris(trifluoromethyl)benzotris(imidazolate); $LiN(CN)_2$; $Li(CF_3CO_2)$; $Li(C_2F_5CO_2)$; $LiCF_3SO_3$; $LiCH_3SO_3$; $LiN(SO_2CF_3)_2$; $LiN(SO_2F)_2$; $LiC(CF_3SO_2)_3$; $LiN(SO_2C_2F_5)_2$; $LiClO_4$; $LiBF_4$; $LiAsF_6$; $LiPF_6$; $LiBF_2(C_2O_4)$; $LiB(C_2O_4)_2$; $LiPF_2(C_2O_4)_2$; $LiPF_4(C_2O_4)$; $LiAsF_6$; $CsF$; $CsPF_6$; $LiN(SO_2CF_3)_2$; $LiN(SO_2F)_2$; $Li_2(B_{12}X_{12-p}H_p)$; $Li_2(B_{10}X_{10-p'}H_{p'})$; or a mixture of any two or more thereof, wherein X may be independently at each occurrence a halogen, p may be 0, 1, 2, 3, 4, 5, 6, 7, 8, 9, 10, 11, or 12, and p' may be 0, 1, 2, 3, 4, 5, 6, 7, 8, 9, or 10.

9. The electrochemical device of claim 1, wherein the lithium salt comprises $LiPF_6$, $LiBF_4$, $LiN(SO_2CF_3)_2$, or $LiN(SO_2F)_2$.

10. The electrochemical device of claim 1 that is a lithium ion battery or a sodium ion battery.

11. The electrochemical device of claim 1, wherein the compound of Formula I is:

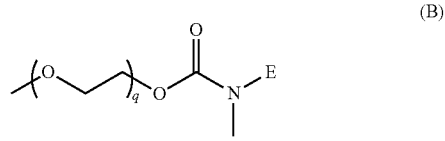

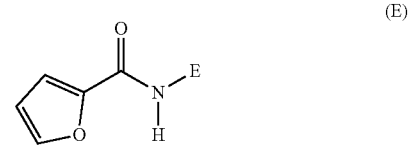

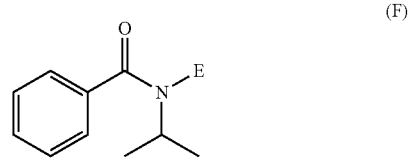

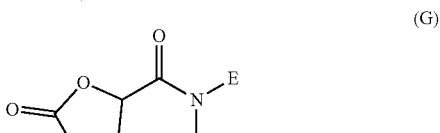

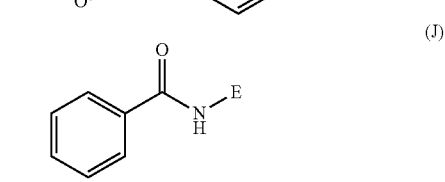

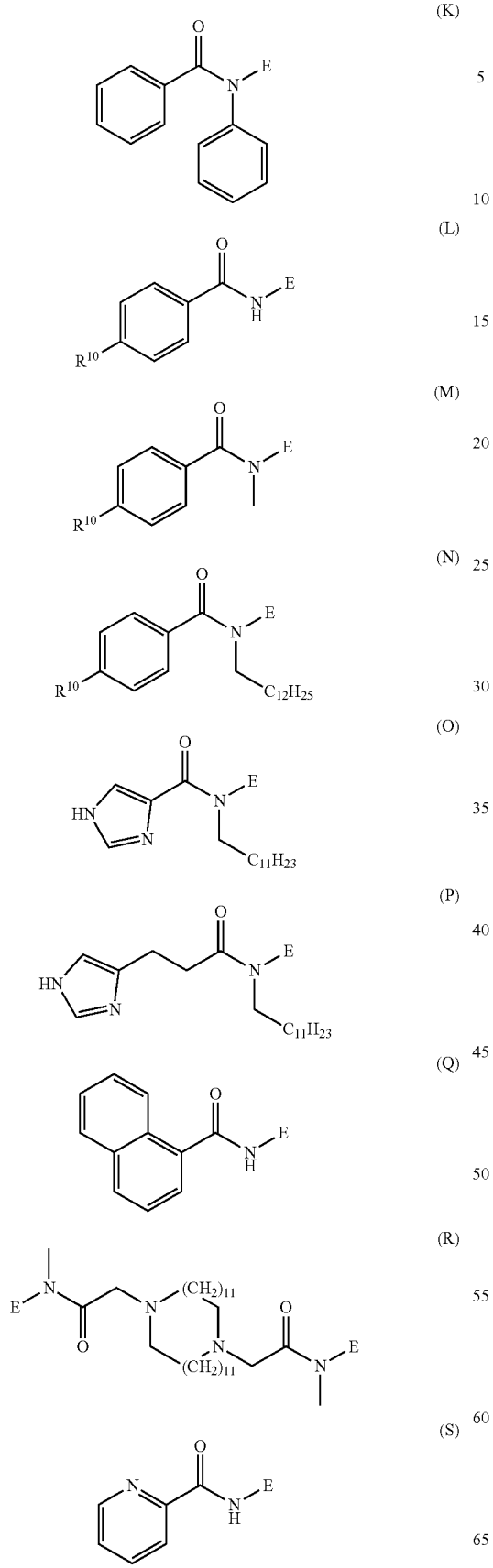
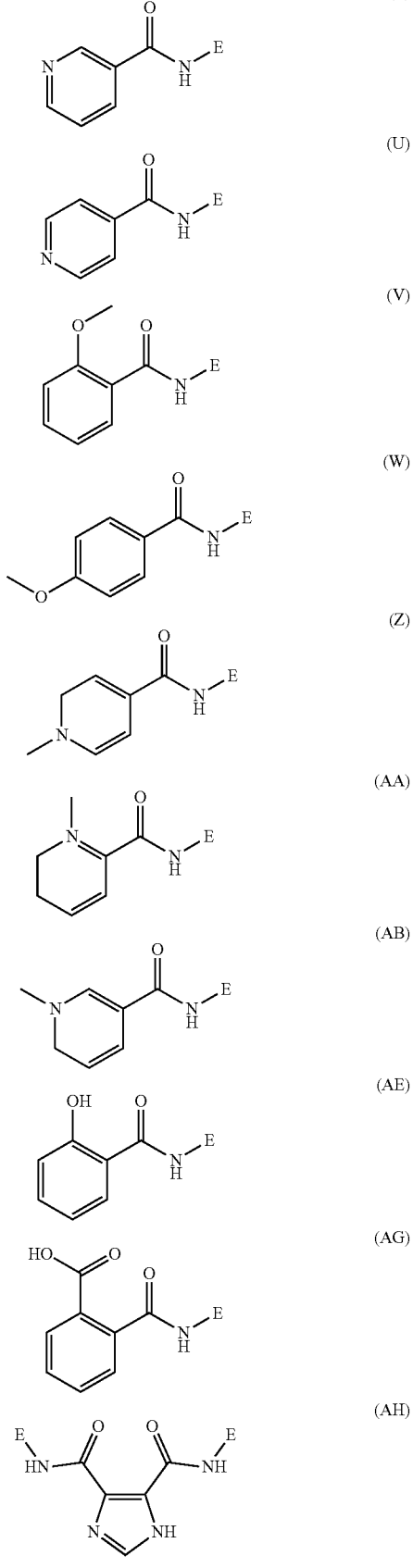

wherein:
  each E is independently —OH, —O—Li⁺, —O—Na⁺, —O—K⁺, or —O—NH₄⁺;
  $R^{10}$ is H, Cl, $NO_2$, or $OCH_3$; and
  each q is from 0 to 20, inclusive.

12. The electrochemical device of claim 11 further comprising a separator between the anode and the cathode.

13. The electrochemical device of claim 11, wherein each E is independently —OH, —O—Li⁺, —O—Na⁺, or —O—K⁺.

\* \* \* \* \*